United States Patent
Lubrano et al.

(10) Patent No.: US 6,294,524 B1
(45) Date of Patent: Sep. 25, 2001

(54) USE OF ERGOSTEROL AND ITS APPARENT COMPOUNDS FOR STIMULATING THE PROLIFERATION OF SKIN CELLS

(75) Inventors: Christian Lubrano, L'Haye-les-Roses; Frederique Poirier, Paris; Jean-Renaud Robin, Nanterre, all of (FR)

(73) Assignee: Laboratoires de Biologies Vegetale Yves Rocher, La Gacilly (FR)

( * ) Notice: Subject to any disclaimer, the term of this patent is extended or adjusted under 35 U.S.C. 154(b) by 0 days.

(21) Appl. No.: 09/508,899
(22) PCT Filed: Sep. 16, 1998
(86) PCT No.: PCT/FR98/01983
§ 371 Date: Oct. 4, 2000
§ 102(e) Date: Oct. 4, 2000
(87) PCT Pub. No.: WO99/13858
PCT Pub. Date: Mar. 25, 1999

(30) Foreign Application Priority Data

Sep. 18, 1997 (FR) .................................................... 97 11655

(51) Int. Cl.[7] ...................................................... A61K 7/48
(52) U.S. Cl. ............................................................. 514/167
(58) Field of Search ............................................... 514/167

(56) References Cited

U.S. PATENT DOCUMENTS 4,338,293 7/1982 Holick .
5,876,709 * 3/1999 Itoh et al. .......................... 424/78.04
6,162,801 * 12/2000 Kita ...................................... 514/167

FOREIGN PATENT DOCUMENTS

| 1594884 | 6/1970 | (FR) . |
| 2734721 | 12/1996 | (FR) . |
| 60 239404 | 11/1985 | (JP) . |
| 07 101835 | 4/1995 | (JP) . |

\* cited by examiner

Primary Examiner—James H. Reamer
(74) Attorney, Agent, or Firm—Young & Thompson

(57) ABSTRACT

The invention concerns the use of compounds of formula (I) in which R represents a linear or branched, substituted or not substituted, saturated or unsaturated $C_1$–$C_{12}$ hydrocarbon chain, for stimulating the proliferation of epidermic cells and fibroblasts.

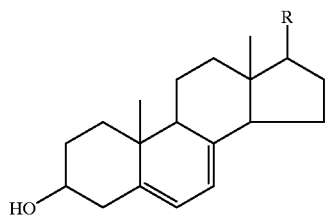

9 Claims, No Drawings

USE OF ERGOSTEROL AND ITS APPARENT COMPOUNDS FOR STIMULATING THE PROLIFERATION OF SKIN CELLS

The present invention relates to the use of compounds of formula I, in particular of natural ergosterol or ergosterol obtained by chemical, enzymatic or biotechnological synthesis, or of a plant extract, such as fungal extract, containing ergosterol, in particular an extract of *Lentinus edodes*, to stimulate the proliferation of epidermal cells and fibroblasts.

Ergosterol, or provitamin D2, is a compound with a steroid ring system containing Δ5 and Δ7 double bonds in its parent ring system and having the following formula:

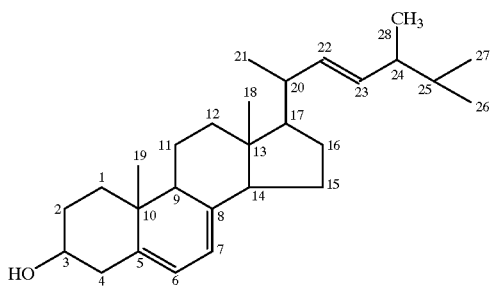

Pure ergosterol is known as an ingredient in cosmetic preparations.

When converted into vitamin D under the action of light, it is used in particular as a precursor of this vitamin in so-called "day" compositions (FR 2 734 721).

On the other hand, the action of ergosterol on the proliferation of epidermal cells and fibroblasts was hitherto unknown.

Ergosterol is naturally present in the plant kingdom, in particular in fungi. Thus, it is present in yeasts and is also abundant in higher fungi such as, in particular, *Lentinus edodes*, also known as Shiitaké.

This is a medicinal and dietary fungus of Asiatic origin. The Japanese name Shiitaké derives from its association with the "shiia" tree, the oak.

This fungus is found in the natural state on trunks of dead trees, in particular on oak trees, ash trees and chestnut trees, and is currently widely cultivated.

The medicinal properties of fungi are mainly linked to one of its polysaccharides, lentinane, by virtue of an immunostimulatory activity, and to eritadenine which has hypocholesterolaemiant activity.

Shiitaké also contains proteins (26% relative to the solids), carbohydrates (65% of solids), minerals (calcium, potassium) and vitamins, in particular vitamins B2 and C.

Moreover, a lipid fraction of Shiitaké has been found to be rich in ergosterol (Ying et al., 1987, Science Press).

The authors of the present invention were interested in the biological properties of ergosterol derivatives, in particular steroid compounds containing a Δ5 double bond and a Δ7 double bond, corresponding to formula I below:

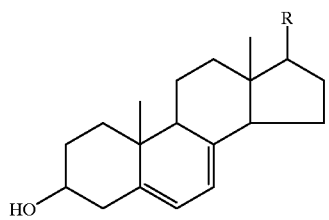

in which R represents a linear or branched, substituted or unsubstituted, saturated or unsaturated $C_1$–$C_{12}$ hydrocarbon-based chain.

The expression "substituted chain" means a hydrocarbon-based chain substituted with one or more substituent groups, in particular such as a hydroxyl group or a $C_1$–$C_8$ alkoxy group.

The expression "unsaturated chain" means a partially or totally unsaturated hydrocarbon-based chain.

They have discovered that these compounds, in particular ergosterol of synthetic origin or in the form of a plant extract, have stimulatory activity on epidermal cells and fibroblasts, thus making them particularly useful in cosmetic compositions intended for combating ageing of the skin and for improving the structural quality of the skin.

One subject of the present invention is thus the use of compounds of formula I as described above to stimulate the proliferation of epidermal cells and fibroblasts.

Among these compounds of formula I, ergosterol, of synthetic or natural origin, is preferentially used.

More particularly, the authors of the present invention have demonstrated that a plant extract, such as a lipid extract of *Lentinus edodes*, also even had an action on the proliferation of epidermal cells and fibroblasts which is higher than the action of pure ergosterol of synthetic origin.

A subject of the present invention is thus the use of ergosterol in the form of a lipid extract of *Lentinus edodes*, to stimulate the proliferation of epidermal cells and fibroblasts.

A subject of the present invention is also a cosmetic composition comprising, besides a vehicle for cosmetic use, a plant extract, such as a fungal extract, containing ergosterol, in particular a lipid extract of *Lentinus edodes*.

Such a plant extract can be obtained by extraction with an apolar or relatively nonpolar solvent or an apolar or relatively nonpolar mixture of solvents chosen in particular from dichloromethane, hexane, ethyl acetate, ethanol and acetone. It can be obtained in particular by extraction in a dichloromethane/ethanol mixture, this mixture being relatively nonpolar overall, in proportions of about 60/about 40 by volume. This extract can also advantageously be obtained using supercritical carbon dioxide and, in this case, is richer in ergosterol.

Preferentially, the compositions according to the invention can comprise from 0.0001 to 0.01% of the said plant extract expressed by weight relative to the weight of the composition.

The cosmetic compositions according to the invention are preferably in the form of a simple oil-in-water or water-in-oil emulsion, or in the form of a multiple emulsion, a microemulsion, an aqueous or aqueous-alcoholic gel, a cream, an oil, an aqueous or aqueous-alcoholic lotion or a stick.

A subject of the present invention is also a cosmetic treatment method which consists in applying to the skin a cosmetic composition as described above.

The action of the compositions according to the invention takes place on the epidermis by increasing the mitotic activity and the renewal of the epidermal cells, resulting in thickening of the epidermis. On the dermis, the compositions according to the invention act by stimulating the fibroblasts, thus accelerating the maturation and cell renewal, which is reflected by increased collagen synthesis, an increase in the water content, an increase in the thickness and an improvement in the elasticity of the skin.

Globally, it appears that an advantageous trophic action can be obtained by applying a cosmetic composition according to the invention, and more particularly maintenance or restoration of the collagen content of the skin.

The examples which follow illustrate the present invention.

EXAMPLE 1

Preparation of the lipid extract of Shiitaké

Dry Shiitaké is reduced to powder form and mixed with solvent (60/40 dichloromethane/methanol) in a proportion of 10% to 20% relative to the solvent and advantageously at a content of 20% (weight/volume).

The powder is extracted under reflux for two hours.

The extract is then filtered and the solvent is evaporated off under vacuum. The residue constitutes the lipid extract of Shiitaké.

The extract can also be prepared by extracting with a supercritical fluid, in particular $CO_2$.

This extraction gives an extract which is richer in ergosterol, not as darkly coloured and with a less pronounced odour than an extract prepared using solvents.

EXAMPLE 2

Assay of the ergosterol

The assay is carried out by HPLC.
a) Materials/reagents required

The following materials and products are used:
MERCK Lichrocart Purospher RP 18 column (5 microns) and precolumn
acetonitrile, methanol and chloroform of analytical grade
Sigma E6510 ergosterol control.
b) Preparation of the mobile phase The 60/40 acetonitrile/methanol mixture (volume/volume, volumes measured separately) is prepared.
c) Preparation of the sample The lipid extract prepared in Example 1 is taken up in a 50/50 (volume/volume) chloroform/methanol mixture. The extract is to be concentrated or diluted according to the results obtained.

Filtration is carried out using a 0.45 µm syringe filter.
d) Procedure
HPLC conditions:
oven temperature: 43° C.
flow rate: 1 ml/min
wavelength: 260 nm
indicative pressure: 70 bar
e) Results A calibration curve is produced using the control substance for an assay. The indicative retention time is about 11 minutes.

The lipid extract obtained using solvents has an ergosterol content of about 5%.

The extract obtained using supercritical $CO_2$ has an ergosterol content of about 9%.

EXAMPLE 3

Tests on cells
a) Materials and methods

The efficacy of the lipophilic phase of the Shiitaké extract obtained using solvents was tested on normal human fibroblasts (13th passage) as a monolayer culture, to visualize the proliferation of the fibroblasts.

The fibroblasts are incubated for 24 hours at 37° C. and at 5% $CO_2$, in 24-well plates, at a density of 8000 cells per $cm^2$. The culture medium is composed of Dulbecco's Modified Eagle Medium without phenol red (DMEM, Gibco, reference 11880028), 10% newborn calf serum (NCS, Gibco, reference 16010084), 100 U/ml of penicillin (Gibco, reference 15140106), 100 µg/ml of streptomycin (Gibco, reference 15140106), 2 mM of glutamine (Gibco, reference 250030024), 0.77 ml of glucose (Gibco, reference 19004019) per 100 ml of final medium and 1% of a solution of non-essential amino acids (Gibco, reference 11140035).

The extract to be tested is placed in contact with the cells in the NCS-poor (2%) culture medium. The test concentration is 0.015 µg/ml ($1.5 \times 10^{-6}$%), the extract being dissolved in ethanol preheated to 60° C.

Positive controls (culture medium containing 10% NCS; β-oestradiol at a concentration of $6 \times 10^{-4}$ µg/ml) and negative controls (culture medium containing 2% NCS) are prepared in parallel.

Similarly, ergosterol is tested at a concentration of $8 \times 10^{-5}$ µg/ml (Sigma).

The measurements are carried out on D1, D2 and D3 by assaying with MTT (Sigma, M5655) which reveals the activity of the mitochondria. The MTT solution is incubated for 3 hours at 37° C. The MTT is then removed and dimethyl sulphoxide (DMSO, Sigma, D 5879) is placed in each well for 10 minutes. After shaking for a few minutes, the reading is taken at 570 nm.
b) Results After treatment for only three days, the extract tested shows a marked stimulation of fibroblast proliferation. In point of fact, at a concentration of $1.5 \times 10^{-6}$%, the lipophilic phase of Shiitaké allows an increase in growth of about 27%, after treatment for 3 days, for fibroblasts at the 13th passage. In the presence of pure ergosterol, the increase in growth is 11% at D3.

In parallel, in the presence of β-oestradiol, a 14% increase in the growth of the fibroblasts is obtained at D3.

Thus, at a dose of lipophilic extract of Shiitaké or of pure ergosterol which is comparable to that of β-oestradiol, equivalent activity, if not higher activity, on the proliferation of human fibroblasts is obtained.

EXAMPLE 4

Comparison of the action of a lipid extract of Shiitaké obtained using solvents (1) and using supercritical $CO_2$ (2)

a) Materials and methods

The lipophilic phase of an extract of Shiitaké obtained by extraction with supercritical $CO_2$ was tested. The protocol for this experiment is identical to that described above. A measurement of the fibroblast proliferation at D7 was also carried out. The effect of the extracts obtained in different manners (using solvents and using supercritical $CO_2$) was compared.

The two extracts were tested at concentrations of 0.015 μg/ml ($1.5 \times 10\%$) and 0.0015 μg/ml ($1.5 \times 10^{-7}\%$), under conditions strictly identical to those previously. In parallel, β-oestradiol and ergosterol were also tested, again under the same conditions.

b) Results

The best results are obtained after treatment for 7 days with the extracts used at a concentration of 0.0015 μg/ml ($1.5 \times 10^{-7}\%$), for the two batches of fibroblasts. However, it appears very clearly that it is the oldest fibroblasts (12th passage) which respond best to the extracts, and more particularly to the lipophilic phase of Shiitaké obtained by extraction with supercritical $CO_2$. Specifically, at this stage, an 18.5% increase in growth can be observed, whereas this increase in growth is only 4% for the younger fibroblasts (6th passage). Also, it should be noted that β-oestradiol and ergosterol produce increases in growth of only 13% and 8%, respectively, at D7 for the oldest fibroblasts; for the youngest fibroblasts, we obtain a 7% increase in growth for β-oestradiol and 2% for ergosterol, again at D7 (cf. table).

|  | Fibroblasts at the 6th passage | Fibroblasts at the 12th passage |
|---|---|---|
| Shiitaké extract 1 $1.5 \times 10^{-7}\%$ | 3% | 11% |
| Shiitaké extract 2 $1.5 \times 10^{-7}\%$ | 4% | 18.5% |
| β-Oestradiol 600 pg/ml | 7% | 13% |
| Ergosterol $8 \times 10^{-5}$ μg/ml | 2% | 8% |

These results are obtained after treatment of the fibroblasts for 7 days with a lipophilic phase of Shiitaké obtained using solvent (No. 1) and a lipophilic phase of Shiitaké obtained by extraction with supercritical $CO_2$ (No. 2).

EXAMPLE 5

Formulae including the lipid extract of Shiitaké a) Example of a composition in the form of an emulsion

| Water | qs |
|---|---|
| Lipid extract of Shiitaké | 0.0001% to 0.01% |
| Preserving agents | qs |
| Propylene glycol | 5.00% |
| Xanthan gum | 0.30% |
| Acrylic/acrylate copolymer | 0.50% |

-continued

| Stearic acid 100 EO** | 3.00% |
|---|---|
| Sorbitan stearate | 2.00% |
| Sorbitan laurate 20 EO | 3.00% |
| Cetylstearyl alcohol | 1.50% |
| Beeswax | 1.00% |
| Wheat germ oil | 5.00% |
| Dimethicone | 2.00% |
| Cyclomethicone | 5.00% |
| Polyacrylamide gel | 2.00% |
| Fragrance | |

**stearic acid with 100 mol of EO b) Example of a composition in the form of a cream

| Water | qs |
|---|---|
| Xanthan gum | 0.30% |
| Sequestering agent (e.g. EDTA) | 0.05% |
| Preserving agents | qs |
| Lipid extract of Shiitaké | 0.0001% to 0.01% |
| C 18 acid | 2.50% |
| C 16 alcohol | 2.50% |
| Trilaurine | 1.00% |
| Karite butter | 3.00% |
| Tocopheryl acetate | 0.05% |
| β-Bisabolol | 0.05% |
| Plant (wheat) oil | 5.00% |
| Dimethicone | 3.00% |
| Polyacrylic acid | 0.30% |
| Water | 3.00% |
| TEA (triethanolamine) | 1.50% |
| Fragrance | 0.10% | c) Example of a composition in the form of a lotion

| Water | qs |
|---|---|
| Sequestering agent | 0.05% |
| Propylene glycol | 2.00% |
| Preserving agents | qs |
| Lipid extract of Shiitaké | 0.0001% to 0.1% |
| Alcohol | 5 to 50% |
| Oleyl alcohol 20 EO | 1.00% |
| Fragrance | 0.05% |
| Dyes | qs |

What is claimed is:

1. A method of stimulating the proliferation of epidermal cells and fibroblasts, comprising applying to human skin an effective amount of a compound of the formula

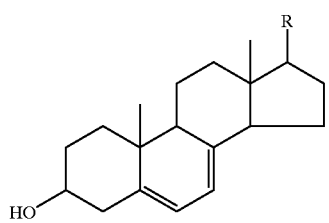

(I)

in which R represents a linear or branched, substituted or unsubstituted, saturated or unsaturated $C_1$–$C_{12}$ hydrocarbon-based chain, said amount being effective to combat aging of the skin or to improve the structural quality of the skin.

2. A method according to claim 1, in which the compound of formula I is ergosterol of synthetic or natural origin.

3. A method according to claim 2, in which the ergosterol is present in the form of a plant extract, containing ergosterol.

4. A method according to claim 3, in which the said extract is a lipid extract of *Lentinus edodes*.

5. A method according to claim 3, in which the plant extract is obtained by extraction with a solvent or a mixture of solvents selected from the group consisting of dichloromethane, hexane, ethyl acetate, ethanol and acetone.

6. A method according to claim 5, in which the plant extract is obtained by extraction in a dichloromethane/ethanol mixture in proportions of about 60/about 40 by volume.

7. A method according to claim 4, in which the said plant extract is obtained by mixing from 10 to 20% by weight of dried *Lentinus edodes* in a solvent.

8. A method according to claim 3, in which the plant extract is obtained by extraction using supercritical carbon dioxide.

9. A method according to claim 3, in which the ergosterol is in the form of a composition comprising from 0.0001 to 0.01% by weight of the said plant extract relative to the weight of the composition.

* * * * *